United States Patent
Mackenzie (10) Patent No.: US 8,551,185 B2
(45) Date of Patent: Oct. 8, 2013

(54) MOUNTING PLATE SYSTEM, VACUUM RESERVOIR PLATE AND ELECTRONIC PUMP SYSTEM FOR PROSTHETIC SOCKET AND RELATED METHODS

(75) Inventor: Craig Mackenzie, Orlando, FL (US)

(73) Assignee: Evolution Industries, Inc., Orlando, FL (US)

( * ) Notice: Subject to any disclaimer, the term of this patent is extended or adjusted under 35 U.S.C. 154(b) by 461 days.

(21) Appl. No.: 12/586,673

(22) Filed: Sep. 25, 2009

(65) Prior Publication Data

US 2010/0094432 A1    Apr. 15, 2010

Related U.S. Application Data

(60) Provisional application No. 61/194,319, filed on Sep. 26, 2008, provisional application No. 61/194,320, filed on Sep. 26, 2008, provisional application No. 61/194,321, filed on Sep. 26, 2008, provisional application No. 61/214,302, filed on Apr. 22, 2009.

(51) Int. Cl.
    *A61F 2/80*      (2006.01)
    *F16K 27/00*      (2006.01)

(52) U.S. Cl.
     USPC ............................ 623/34; 251/357

(58) Field of Classification Search
     USPC ........................... 623/34; 251/357
     See application file for complete search history.

(56) References Cited

U.S. PATENT DOCUMENTS

| | | |
|---|---|---|
| 980,457 A | 1/1911 | Toles |
| 1,398,824 A | 11/1921 | Abrams |
| 1,893,853 A | 1/1933 | Tullis |
| 2,530,285 A | 11/1950 | Catranis |
| 2,533,404 A | 12/1950 | Sharp et al. |
| 2,634,424 A | 4/1953 | Gorman |
| 2,671,225 A | 3/1954 | Schoene et al. |
| 2,808,593 A | 10/1957 | Andersen |
| 3,393,407 A | 7/1968 | Kandel |
| 3,671,980 A | 6/1972 | Baird |
| 4,923,474 A | 5/1990 | Klasson et al. |
| 5,007,937 A | 4/1991 | Fishman et al. |
| 5,139,523 A | 8/1992 | Paton et al. |
| 5,163,965 A | 11/1992 | Rasmusson et al. |

(Continued)

FOREIGN PATENT DOCUMENTS

| | | |
|---|---|---|
| DE | 745 981 | 5/1944 |
| DE | 813 190 | 7/1949 |

(Continued)

*Primary Examiner* — David H Willse
(74) *Attorney, Agent, or Firm* — Workman Nydegger (57) ABSTRACT

The mounting plate system is for use with a prosthetic socket, the socket having at least one aperture in a distal end thereof and in fluid communication with an interior portion of the socket which receives a residual limb. The mounting plate system includes a mounting plate having a top face to interface with the socket, and a bottom face for attachment to lower portions of a prosthetic limb. An opening in the mounting plate extends from the top face to the bottom face thereof, and a valve housing is positioned in the opening and has a channel therein for fluid communication with the interior portion of the socket via the at least one aperture. A one-way expulsion valve is secured between the valve housing and the socket adjacent the aperture and for regulating fluid communication between the interior portion of the socket and the channel in the valve housing. A vacuum reservoir seal plate is also provided.

20 Claims, 4 Drawing Sheets

(56) References Cited

U.S. PATENT DOCUMENTS

| | | | |
|---|---|---|---|
| 5,226,918 A | 7/1993 | Silagy et al. | |
| 5,314,496 A | 5/1994 | Harris et al. | |
| 5,376,129 A | 12/1994 | Faulkner et al. | |
| 5,376,131 A | 12/1994 | Lenze et al. | |
| 5,549,709 A | 8/1996 | Caspers | |
| 5,593,454 A | 1/1997 | Helmy | |
| 5,658,353 A | 8/1997 | Layton | |
| 5,662,715 A | 9/1997 | Slemker | |
| 5,702,489 A | 12/1997 | Slemker | |
| 5,718,925 A | 2/1998 | Kristinsson et al. | |
| 5,728,170 A | 3/1998 | Becker et al. | |
| 5,735,906 A | 4/1998 | Caspers | |
| 5,888,216 A | 3/1999 | Haberman | |
| 5,904,722 A | 5/1999 | Caspers | |
| 5,931,872 A | 8/1999 | Lohmann | |
| 5,972,036 A | 10/1999 | Kirstinsson et al. | |
| 6,063,125 A * | 5/2000 | Arbogast et al. | 623/34 |
| 6,149,691 A | 11/2000 | Fay et al. | |
| 6,231,616 B1 | 5/2001 | Helmy | |
| 6,231,617 B1 | 5/2001 | Fay | |
| 6,273,918 B1 | 8/2001 | Yuhasz et al. | |
| 6,287,345 B1 | 9/2001 | Slemker et al. | |
| 6,361,568 B1 | 3/2002 | Hoerner | |
| 6,508,842 B1 | 1/2003 | Caspers | |
| 6,554,868 B1 | 4/2003 | Caspers | |
| 6,585,774 B2 | 7/2003 | Dean, Jr. et al. | |
| 6,645,253 B2 | 11/2003 | Caspers | |
| 6,726,726 B2 | 4/2004 | Caspers | |
| 6,761,742 B2 | 7/2004 | Caspers | |
| 7,056,303 B2 * | 6/2006 | Dennis et al. | 604/167.03 |
| 7,235,108 B2 | 6/2007 | Carstens | |
| 7,427,297 B2 | 9/2008 | Patterson et al. | |
| 7,771,487 B2 | 8/2010 | Mantelmacher | |
| 8,211,187 B2 | 7/2012 | Slemker | |
| 2001/0005798 A1 | 6/2001 | Caspers | |
| 2001/0016781 A1 | 8/2001 | Caspers | |
| 2002/0040248 A1 | 4/2002 | Karason | |
| 2002/0087215 A1 | 7/2002 | Caspers | |
| 2002/0091449 A1 | 7/2002 | Caspers et al. | |
| 2002/0099450 A1 | 7/2002 | Dean, Jr. et al. | |
| 2003/0191539 A1 | 10/2003 | Caspers | |
| 2004/0030411 A1 | 2/2004 | Caspers | |
| 2004/0098136 A1 | 5/2004 | Caspers | |
| 2004/0122528 A1 | 6/2004 | Egilsson | |
| 2004/0143345 A1 | 7/2004 | Caspers | |
| 2004/0167638 A1 | 8/2004 | Caspers | |
| 2004/0181290 A1 | 9/2004 | Caspers | |
| 2004/0236434 A1 | 11/2004 | Carstens | |
| 2004/0243251 A1 | 12/2004 | Carstens | |

FOREIGN PATENT DOCUMENTS

| | | | |
|---|---|---|---|
| DE | 1 795 809 | 9/1959 | |
| DE | 2 060 239 | 6/1972 | |
| DE | 25 40 138 | 3/1977 | |
| DE | 27 29 800 A1 * | 1/1979 | 623/34 |
| DE | 32 21 920 A1 | 4/1983 | |
| DE | 35 08 919 A1 | 9/1986 | |
| DE | 94 19 208.1 U1 | 11/1994 | |
| GB | 267 988 | 9/1925 | |
| GB | 2 069 847 A | 9/1981 | |
| GB | 2 087 727 A | 6/1982 | |
| JP | 07-155343 A | 6/1995 | |
| WO | 00/74611 A2 | 12/2000 | |
| WO | 01/54631 A1 | 8/2001 | |
| WO | 03/024367 A2 | 3/2003 | |
| WO | 03/024370 A1 | 3/2003 | |
| WO | 03/039398 A1 | 3/2003 | |
| WO | 03/099173 A1 | 12/2003 | |

\* cited by examiner

MOUNTING PLATE SYSTEM, VACUUM RESERVOIR PLATE AND ELECTRONIC PUMP SYSTEM FOR PROSTHETIC SOCKET AND RELATED METHODS

CROSS-REFERENCE TO RELATED APPLICATIONS

This application claims the benefit of U.S. provisional application Nos. 61/194,319, 61/194,320 and 61/194,321 filed Sep. 26, 2008, and U.S. provisional application No. 61/214,302, filed Apr. 22, 2009, which are incorporated by reference in their entirety.

BACKGROUND OF THE INVENTION (1) Field of the Invention

The present invention relates to the field of prosthetics, and more particularly to vacuum assisted prosthetic sockets and related methods.

(2) Discussion of Related Art

Amputees use prosthetic devices on their residual limbs using various vacuum or suction arrangements that include the use of liners that are worn between the residual limb and the prosthetic socket. When an amputee walks air inside the socket allows the socket to fall away from the amputee during swing phase (the time the prosthesis is in the air between steps) causing an accelerated impact of the residual limb and the bottom of the socket when the heel hits the floor. By removing the air in the socket the prosthesis is held closer to the residual limb during swing phase reducing the accelerated impact at heel strike. There are many ways to remove the air and several different expulsion valves on the market. Most are installed in the walls of the socket. This is not the most appropriate placement. A valve housed in the distal or bottom of the socket will expel the most air as the amputee's weight at heel strike is directed downward towards the distal portion of the socket.

A known configuration includes the use of a one-way valve provided at a distal end of a socket so that air between the distal end of the residual limb may be pushed through the one-way valve until the residual limb and associated liner are fully inserted into the socket. The one-way valve is then in a closed condition.

To maintain the sub-atmospheric pressure or vacuum at the distal end of the socket, sealing sleeves and other arrangements may be used to prevent influx of air around the distal end of the residual limb and into the distal end of the socket. With a vacuum suspension system, any significant loss of vacuum may result in separation of the prosthetic socket from the residual limb.

Providing a vacuum reservoir chamber maintained at sub-atmospheric pressure and in communication with a prosthetic socket may aid in maintaining a partial vacuum within the socket to compensate for variations in volume of the residual limb while the prosthetic socket is worn and to compensate for air leakage around the residual limb. An integrated system may include vacuum pressure sensors and an evacuation device carried by the prosthetic socket.

U.S. published patent application No. 2004/0260403 to Patterson et al. provides an integrated vacuum chamber socket system without any additional electronics (e.g. sensors, pump etc.) to maintain the vacuum within the chamber. However, this configuration may result in leakage of air into the socket that can reduce the vacuum within the vacuum chamber. Also, U.S. published patent application No. 2008/0086218discloses a vacuum chamber socket system that includes a rigid shell or socket having an integrated vacuum reservoir chamber that may be distally located and that shares a distal common wall with a receiving portion of the socket. The common wall includes a vacuum transfer port having a one-way or non-return valve disposed therein which allows the receiving portion to communicate with the chamber. Such systems require a complicated manufacturing process to form the integrated chamber and the patient may need special skills to don the socket.

Further, there are many different types of one-way valves including spring and duckbill type valves. Spring valves use a spring to resist the air from traveling in one direction while allowing it to travel in the other. The disadvantage to spring valves is the air must accumulate enough force to over power the spring and open the valve. The consequence of this is that the spring will close the valve before most of the air escapes the socket. This is called cracking pressure. The lowest limit for spring expulsion valves used in prosthetics is about 2 psi.

BRIEF SUMMARY OF THE INVENTION

It is an object of the present invention to provide a mounting plate system, vacuum reservoir plate system and/or electronic pump system, and associated methods, for use with prosthetic sockets and having improved features and reliability including the reduction or elimination of leaks and/or maintaining of an adequate level of vacuum within the systems.

This and other objects, advantages and features in accordance with the present invention are provided by a mounting plate system for use with a prosthetic socket, the socket having at least one aperture in a distal end thereof and in fluid communication with an interior portion of the socket which receives a residual limb. The mounting plate system comprising: a mounting plate having a top face to interface with the socket, and a bottom face for attachment to lower portions of a prosthetic limb; an opening in the mounting plate extending from the top face to the bottom face thereof; a valve housing positioned in the opening and having a channel therein for fluid communication with the interior portion of the socket via the at least one aperture; and a one-way expulsion valve secured between the valve housing and the socket adjacent the aperture and for regulating fluid communication between the interior portion of the socket and the channel in the valve housing.

The bottom face of the mounting plate preferably includes a pattern of threaded holes for attachment to lower portions of the prosthetic limb. The opening in the mounting plate may comprise a threaded opening; and wherein the valve housing then comprises a threaded portion for threaded engagement with the threaded opening in the mounting plate. The one-way expulsion valve may be a rubber duckbill valve, and may extend into the channel in the valve housing. A valve housing o-ring may be provided for sealing engagement between the valve housing and adjacent portions of the opening in the mounting plate.

Other objects, advantages and features in accordance with the present invention are provided by a mounting plate for use with a prosthetic socket, the socket having at least one aperture in a distal end thereof and in fluid communication with an interior portion of the socket which receives a residual limb. The mounting plate comprises a top face to interface with the socket, a bottom face for attachment to lower portions of a prosthetic limb, and a valve housing threaded opening extending from the top face to the bottom face to receive a valve housing in threaded engagement therewith. Again, the bottom face may include a pattern of threaded holes for attachment to lower portions of the prosthetic limb.

Other objects, advantages and features in accordance with the present invention are provided by a method of providing a mounting plate system for use with a prosthetic socket, the socket having at least one aperture in a distal end thereof and in fluid communication with an interior portion of the socket which receives a residual limb. The method includes providing a mounting plate having a top face to interface with the socket, and a bottom face for attachment to lower portions of a prosthetic limb. An opening is provided in the mounting plate extending from the top face to the bottom face thereof, and the method includes positioning a valve housing in the opening and having a channel therein for fluid communication with the interior portion of the socket via the at least one aperture. The method further includes securing a one-way expulsion valve between the valve housing and the socket adjacent the aperture and for regulating fluid communication between the interior portion of the socket and the channel in the valve housing.

The method may further include providing a dummy valve housing in the opening of the mounting plate and then bonding the top face of the mounting plate to the distal end of the socket to create a flat mating surface on the distal end of the socket for a flange of the one-way expulsion valve, the dummy valve housing including a drill guide therein. Furthermore, the method may then include laminating the mounting plate to the socket, drilling a hole through the drill guide in the dummy valve housing to the interior portion of the socket to define the aperture, removing the dummy valve housing, positioning the one-way expulsion valve within the opening in the mounting plate, and securing the one-way expulsion valve in place with the valve housing positioned in the opening of the mounting plate and compressing the flange thereof against the flat mating surface of the socket.

Objects and features of the present invention are also provided by a vacuum reservoir seal plate system and associated methods including the features described below.

Thus, with the present approach, it is possible to provide for secure attachment of lower prosthetic limb portions to the socket while reducing and/or eliminating leaks within the mounting plate system.

DETAILED DESCRIPTION OF THE PREFERRED EMBODIMENTS

The present invention will now be described more fully hereinafter with reference to the accompanying drawings, in which preferred embodiments of the invention are shown. The approach of the invention may be embodied in many different forms and should not be construed as limited to the embodiments set forth herein. Rather, the embodiments are provided so that this disclosure will be thorough and complete, and will fully convey the scope of the invention to those skilled in the art.

Embodiments of the invention may be incorporated into different prosthetic appliances. Some examples include above and below knee lower limb prosthetics, as well as upper limb prosthetics. While the advantages of the vacuum assisted system may be discussed in detail herein with respect to lower limb prosthetics, similar advantages may be achieved when the features of the present invention are applied to upper limb prosthetics.

Figure 1:
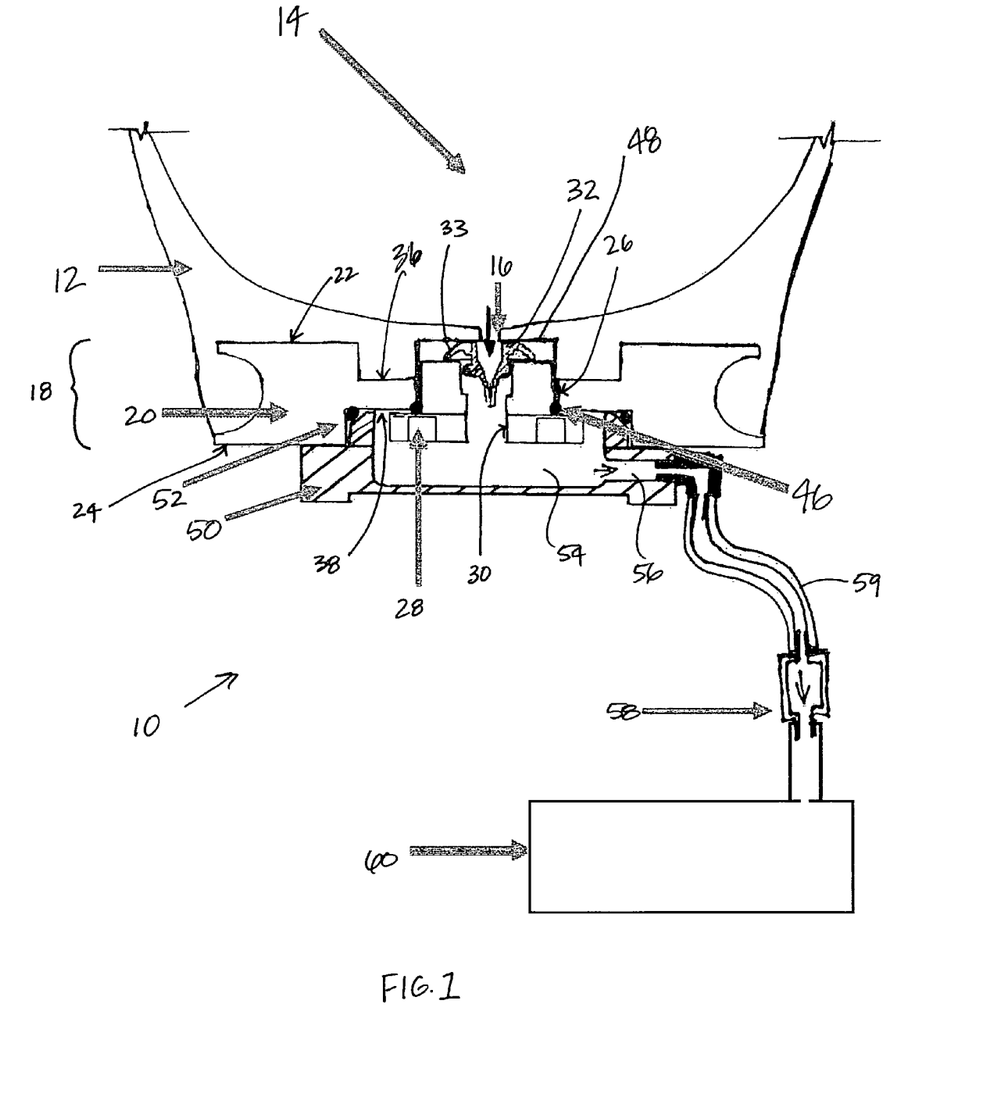
FIG. 1 is a cross-sectional view of a mounting plate system, vacuum reservoir plate system and electronic pump system in connection with a prosthetic socket, and in accordance with features of the present invention.
Figure 2A:
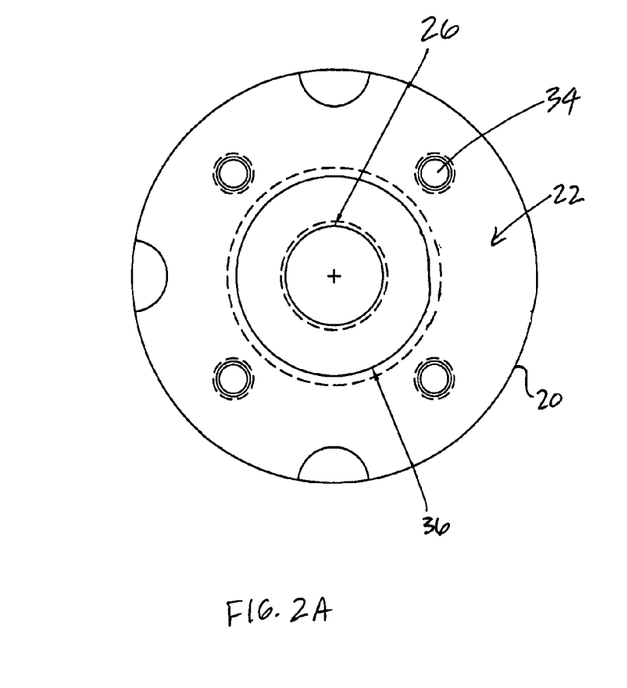
FIGS. 2A-2C are additional views of the mounting plate of the system of FIG. 1.
Figure 2B:
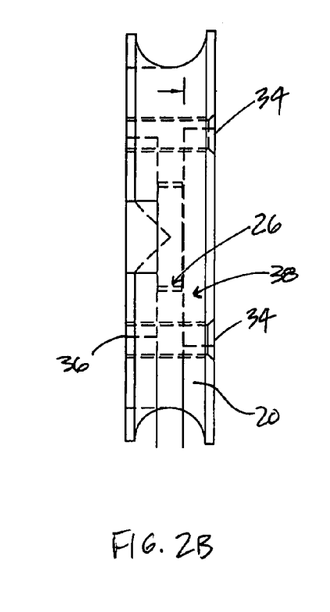
Figure 2C:
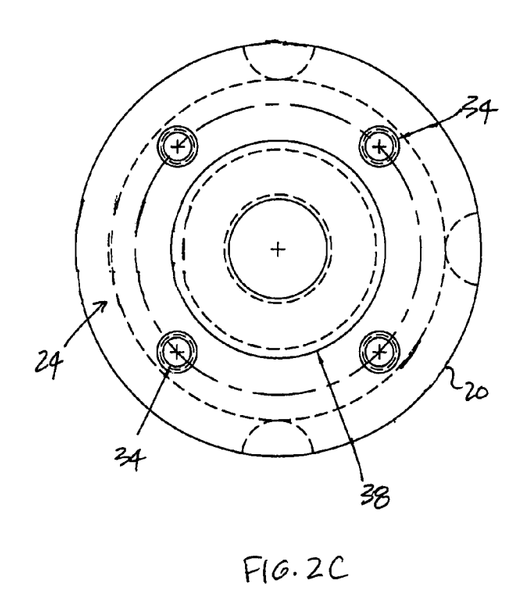
Figure 3A:
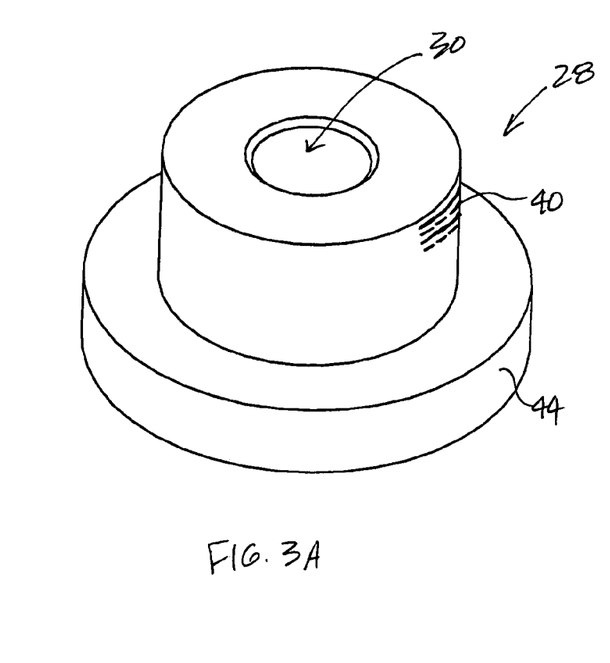
FIGS. 3A-3C are additional views of the valve housing of the system of FIG. 1.
Figure 3B:
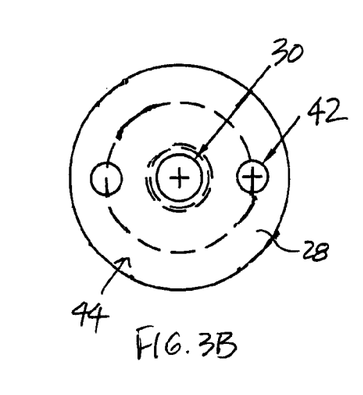
Figure 3C:
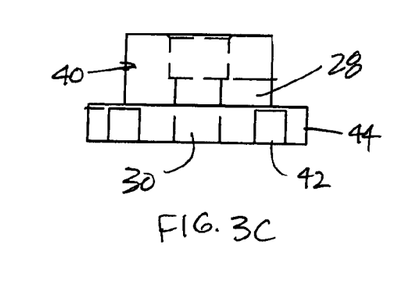
Figure 4A:
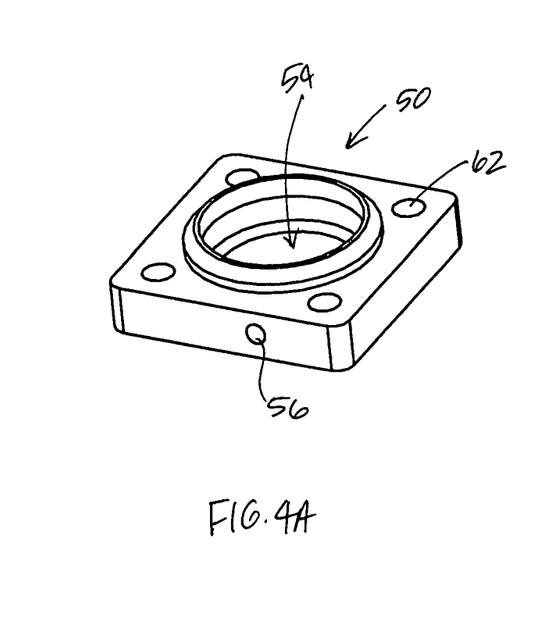
FIGS. 4A-4C are additional views of the vacuum reservoir plate of the system of FIG. 1.
Figure 4B:
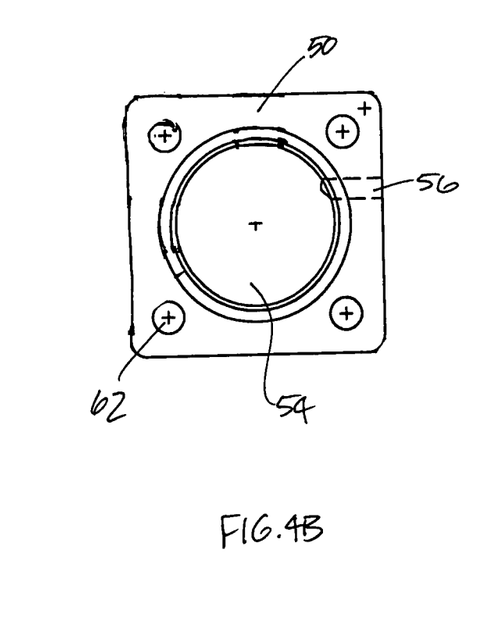
Figure 4C:
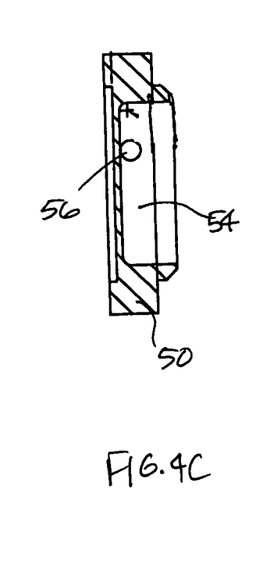

Referring to FIGS. 1-4 below, embodiments consistent with features of the present invention will be described. In FIG. 1, a vacuum assisted system 10 is for use with a prosthetic socket that includes a socket wall 12 defining a socket interior 14 for receiving a residual limb therein, as is appreciated by those skilled in the art. The socket also has at least one aperture 16 in a distal end thereof and in fluid communication with the interior portion 14 of the socket.

A mounting plate system 18 includes a mounting plate 20 having a top face 22 to interface with the socket, and a bottom face 24 for attachment to lower portions of a prosthetic limb. An opening 26 in the mounting plate 20 extends from the top face 22 to the bottom face 24 thereof. A valve housing 28 is positioned in the opening 26 and has a channel 30 therein for fluid communication with the interior portion 14 of the socket via the at least one aperture 16. A one-way expulsion valve 32 is secured between the valve housing 28 and the socket adjacent the aperture 16 and for regulating fluid communication between the interior portion 14 of the socket and the channel 30 in the valve housing 28.

The bottom face 24 of the mounting plate 20 preferably includes a pattern of threaded holes 34 (e.g. with a standard pattern of threaded holes as appreciated by those skilled in the art) for attachment to lower portions of the prosthetic limb. The mounting plate may also include top and bottom recesses 36 and 38 that extend from a respective surface of the mounting plate and surround the opening 26.

The opening 26 in the mounting plate 20 may be a threaded opening, and the valve housing 28 may then include a threaded portion 40 for threaded engagement with the threaded opening in the mounting plate 20. Various recesses 42 may also be provided in the shoulder portion 44 of the valve housing 28 to receive a corresponding projection of a tool to assist in tightening the valve housing 28 in the threaded opening 26 of the mounting plate 20.

The one-way expulsion valve 32 may be a rubber duckbill valve, and may extend into the channel 30 in the valve housing 28, e.g. as illustrated in FIG. 1. The rubber duckbill valve preferably has a low cracking pressure, about 0.2 psi. A valve housing o-ring 46 may be provided for sealing engagement between the valve housing 28 and adjacent portions of the opening 26 in the mounting plate 20. This arrangement results in more air being expelled from the socket to decrease the space between the distal end of the amputee's residual limb and the bottom of the socket, e.g. reducing the accelerated impact at heel strike, making the socket more comfortable for the amputee.

Another benefit of the arrangement in accordance with features of the present invention is that the valve housing 28 compresses the flange 33 on the duckbill valve 32 between the socket lamination and the valve housing 28, reducing or eliminating any leak that could occur between the valve housing 28 and the mounting plate 20. The connection between the socket lamination and the mounting plate 20 is purely physical and during ambulation the mounting plate 20 may be subjected to non-linear forces that will cause the mounting plate and the socket lamination to at least partially separate. This may not be evident to the amputee and does not compromise the strength of the socket but would allow air to pass between the mounting plate 20 and the socket lamination into the interior 14 of the socket if not for the sealing approach of the present invention. Ordinarily, such a leak would compromise the socket fit. Conventional valve arrangements that are housed in the distal portion of the socket do not adequately seal for this type of leak.

The sealing face 48 for the valve 32 in the lamination may be accomplished during the manufacturing process of the laminated socket. A dummy valve housing is inserted in the mounting plate 20 and the mounting plate is then bonded onto the bottom of a thin plastic sheet that has been formed over the positive cast representing the inner shape of the final socket. The bond is made from a resin mixed with a thickening agent to produce the correct consistency to fill the threads of the dummy valve housing and produce the flat mating surface 48 for the valve flange 33 on the bottom of the laminated socket. Once the bonding material has set, the mounting plate 20 is further attached to the plastic sheet by several layers of carbon fiber and fiberglass, for example, as would be appreciated by the skilled artisan. Once the lamination has set, a hole is drilled though a drill guide in the dummy valve housing to the interior portion of the socket to define the aperture 16. The dummy valve housing is then removed and the valve 32 and valve housing 28 are then inserted, via the opening 26 in the mounting plate 20, into the pocket that has been created in the distal end of the socket. This process creates an ideal seal between the valve 32 and the lamination, reducing or eliminating any leaks between the mounting plate 20 and lamination.

A seal plate 50 may be provided for removable attachment (e.g. via a threaded engagement) to the mounting plate 20 adjacent the valve housing 28. Again, a seal plate o-ring 52 may be provided between the seal plate 50 and the mounting plate 20 to ensure a seal therebetween. The seal plate 50 may include a vacuum reservoir 54 therein in regulated fluid communication with the interior portion 14 of the socket via the valve housing channel 30, the socket aperture 16 and the one-way expulsion valve 32. The seal plate 50 may include a port 56 for direct or indirect connection to a vacuum pump 60, such as an electronic vacuum pump. Such a pump 60 may be connected to the seal plate port 56 via a second one-way valve 58 and/or an associated conduit 59, such as a flexible tube. The seal plate 50 may include through holes 62 (e.g. threaded) that match the patterned threaded holes 34 of the mounting plate 20 for assisting in the attachment of the lower portions of the prosthetic limb.

When vacuum is applied to the second one-way valve 58, air is removed from the seal plate 50 creating a vacuum in the vacuum reservoir 54, between the seal plate 50 and the mounting plate 20. When enough vacuum has accumulated in the seal plate 50, the one-way expulsion valve 32 in the valve housing 28 opens and allows air to be drawn from the socket interior 14 into the seal plate 50 and then evacuated from the seal plate through the seal plate one-way valve 58. Air can be evacuated through the one-way seal plate valve 58 in several different ways including a hand pump, electronic pump, or mechanical pump activated by the motion of the patient walking, for example.

As all sockets may leak, the vacuum reservoir 54 contained in the seal plate 50 reduces the affect of the leak and may allow the amputee to maintain some level of vacuum for the entire day without the need to regenerate the level of vacuum within the seal plate 50. This is beneficial for amputees utilizing hand pumps or an external electric pump 60. Electronic pumps that are housed within a prosthetic device and that are activated by computer control when the level of vacuum drops below a certain level would also benefit from this technology. Although the electronic vacuum pump would initially be activated for a longer duration, the pump would not activate as frequently with such a reservoir arrangement, thus extending the battery life of the electronic pump.

The one-way expulsion valve 32 is placed between the socket and the seal plate 50 so that in the event of a leak, any air in the seal plate 50 could not enter the socket environment and compromise the amputee's suspension. In this case, the one-way expulsion valve 32 in the mounting plate 20 would expel air in the socket via the force created by the patients weight during the normal gait cycle.

As discussed above, the mounting plate one-way expulsion valve 32 is sealed to the socket wall by being compressed between the valve housing 28 and the socket wall 48, the valve housing 28 is sealed to the mounting plate 20 by an o-ring 46, and the seal plate 50 is sealed to the mounting plate 20 by an o-ring 52. These three seals ensure that the only air that can enter the system is from the socket interior 14.

The addition of an electronic pump 60 to the seal plate 50 eliminates the need for the amputee to use and external vacuum source to remove the air from the reservoir 54. The electronic vacuum pump 60 can be built as a structural component or a stand-alone unit that is attached to the prosthetic device in some non-load bearing manner. The electronic vacuum pump 60 is designed to work in tandem with the seal plate 50. The electronic vacuum pump's programming, as set in its circuitry, allows it to maintain a certain level of vacuum in the seal plate vacuum reservoir 54 through the second one-way valve 58. The seal plate 50 then regulates vacuum in the amputee's socket environment through the one-way expulsion valve 32 between the seal plate 50 and the socket. As such, air is prevented from traveling backwards through the system. The system may be used with or without the vacuum reservoir 54 in the seal plate 50 as may be desired.

The seal plate may also define the cover or lid of an enclosure that houses the pump and various electronics. The electronic components may include a programmable controller (e.g. a microprocessor), a vacuum pump, a battery, and a vacuum sensor. The system may also contain an accelerometer or gyroscope and battery protection circuitry. Other sensors and features may be added, as they are deemed necessary. A wireless transceiver and/or a wired communications port may be associated with the controller for communication with external devices.

The accelerometer senses motion in the prostheses, turning on the vacuum sensor. The sensor sends information about the vacuum status in the seal plate and compares it with the set low vacuum value. If the vacuum in the seal plate is higher than the set low vacuum value the controller does nothing. If the vacuum is lower than the set low vacuum value then the processor activates the vacuum pump. The vacuum pump remains on until the vacuum sensor meets a set high vacuum value. Once the set high vacuum value has been reached, the controller shuts off the vacuum pump.

Various safeguards and sleep mode may include: if the vacuum pump runs for longer than a set period of time without an increase in vacuum level, the controller will shut off the vacuum pump; if the accelerometer does not detect motion in the prostheses for a set period of time the controller will enter sleep mode and not activate the vacuum sensor or vacuum pump.

Additional circuitry and software may allow the controller to communicate with a computer, wirelessly or otherwise, to allow the prosthetist or patient to set the high and low vacuum values, sleep times or other functions and allow for the accumulation of data over a given period of time. To lessen office visits the controller may be connected to a network (e.g. the internet) and/or e-mail service for the purpose of remotely providing the prosthetist with information on system status or transfer of data collected over a period of time. Such information could include number of steps per day, vacuum levels, battery condition or a number of other data sets that could help the prosthetist evaluate the health of the patient and the condition of the prosthesis.

Advantages of the above described embodiments include: 1) reduces or prevents any leaks between the mounting plate and the lamination; 2) maintains a level of vacuum longer than systems without reservoirs; 3) in the event of a leak does not allow air to travel freely into the socket environment; 4) may be manufactured as a component; and 5) allows for automatic regulation of the socket environment.

The present invention was described with references to preferred embodiments of the invention. This invention may, however, be embodied in many different forms and should not be construed as limited to the specific embodiments set forth herein. Rather, these embodiments are provided so that this disclosure will be thorough and complete, and will fully convey the scope of the invention to those skilled in the art. Many modifications and other embodiments of the invention will come to the mind of one skilled in the art having the benefit of the teachings presented in the foregoing descriptions and the associated drawings.

The invention claimed is:

1. A mounting plate system for use with a prosthetic socket, the socket having at least one aperture in a distal end thereof and in fluid communication with an interior portion of the socket which receives a residual limb, the mounting plate system comprising:
   a mounting plate having a top face arranged to be directly adjacent to a distal outer periphery of the socket, and a bottom face for attachment to lower portions of a prosthetic limb;
   an opening in the mounting plate extending from the top face to the bottom face thereof, and a bottom recess in the mounting plate extending from the bottom face and surrounding the opening;
   a valve housing positioned in the opening and having a channel therein for fluid communication with the interior portion of the socket via the at least one aperture, the valve housing further having a shoulder portion arranged to abut the bottom recess in the mounting plate; and
   a one-way expulsion valve arranged to be removably secured directly between and against the valve housing and the socket distal outer periphery adjacent the aperture and for regulating fluid communication between the interior portion of the socket and the channel in the valve housing, the valve housing arranged for compressing a flange of the one-way expulsion valve against the distal outer periphery of the socket to form a seal therewith.

2. The mounting plate system according to claim 1, wherein the bottom face of the mounting plate includes a pattern of threaded holes for attachment to lower portions of the prosthetic limb.

3. The mounting plate system according to claim 1, wherein the opening in the mounting plate comprises a threaded opening; and wherein the valve housing comprises a threaded portion for threaded engagement with the threaded opening in the mounting plate.

4. The mounting plate system according to claim 1, wherein the one-way expulsion valve comprises a rubber duckbill valve.

5. The mounting plate system according to claim 4, wherein the duckbill valve extends into the channel in the valve housing.

6. The mounting plate system according to claim 1, further comprising a valve housing o-ring for sealing engagement between the valve housing and adjacent portions of the opening in the mounting plate.

7. The mounting plate system according to claim 1, further comprising a seal plate arranged to removably secure to the bottom face of the mounting plate, and surround a lower surface of the valve housing.

8. The mounting plate system according to claim 1, wherein the one-way expulsion valve is positionable below the at least one aperture.

9. The mounting plate system according to claim 1, wherein the channel has at least first and second diameters formed along its length, the first diameter being greater than the second diameter and adapted to receive at least a portion of the one-way valve.

10. The mounting plate system according to claim 1, wherein an upper surface of the valve housing is arranged to form a clearance between the distal outer periphery of the socket when secured to the mounting plate.

11. A mounting plate system for use with a prosthetic socket, the socket having at least one aperture in a distal end thereof and in fluid communication with an interior portion of the socket which receives a residual limb, the mounting plate system comprising:
   a mounting plate having a top face arranged to be directly adjacent to a distal outer periphery of the socket, side walls arranged to be surrounded by portions of the socket so as to be secured therewith, and a bottom face for attachment to lower portions of a prosthetic limb;
   an opening defined by the mounting plate extending from the top face to the bottom face thereof, and a bottom recess in the mounting plate extending from the bottom face and surrounding the opening;
   a valve housing positioned in the opening and having a channel therein for fluid communication with the interior portion of the socket via the at least one aperture, the valve housing defining a shoulder portion arranged to abut the bottom recess in the mounting plate, and an upper surface of the valve housing being arranged to form a clearance between the distal outer periphery of the socket when secured to the mounting plate; and
   a one-way expulsion valve arranged to be sealingly secured directly between the valve housing and the socket distal outer periphery and within the clearance, the expulsion valve arranged for regulating fluid communication between the interior portion of the socket and the channel in the valve housing.

12. The mounting plate system according to claim 11, wherein the opening in the mounting plate comprises a threaded opening; and wherein the valve housing comprises a threaded portion for threaded engagement with the threaded opening in the mounting plate.

13. The mounting plate system according to claim 11, wherein the one-way expulsion valve comprises a rubber duckbill valve.

14. The mounting plate system according to claim 11, further comprising a seal plate arranged to removably secure to the bottom face of the mounting plate, and surround a lower surface of the valve housing.

15. The mounting plate system according to claim 11, wherein the one-way expulsion valve is positionable below the at least one aperture.

16. The mounting plate system according to claim 11, wherein the channel has at least first and second diameters formed along its length, the first diameter being greater than the second diameter and adapted to receive at least a portion of the one-way valve.

17. A mounting plate system for use with a prosthetic socket, the socket having at least one aperture in a distal end thereof and in fluid communication with an interior portion of the socket which receives a residual limb, the mounting plate system comprising:
   a mounting plate having a top face arranged to be directly adjacent to a distal outer periphery of the socket, and a bottom face for attachment to lower portions of a prosthetic limb;
   an opening in the mounting plate extending from the top face to the bottom face thereof;
   a valve housing positioned in the opening and having a channel therein for fluid communication with the interior portion of the socket via the at least one aperture; and
   a one-way expulsion valve arranged to be removably secured directly between and against the valve housing and the socket distal outer periphery adjacent the aperture and for regulating fluid communication between the interior portion of the socket and the channel in the valve housing, wherein the one-way expulsion valve is positionable below the at least one aperture;
   a seal plate arranged to removably secure to the bottom face of the mounting plate, and surround a lower surface of the valve housing.

18. The mounting plate system according to claim 17, wherein the opening in the mounting plate comprises a threaded opening; and wherein the valve housing comprises a threaded portion for threaded engagement with the threaded opening in the mounting plate.

19. The mounting plate system according to claim 17, wherein the channel has at least first and second diameters formed along its length, the first diameter being greater than the second diameter and adapted to receive at least a portion of the one-way valve.

20. The mounting plate system according to claim 17, wherein the valve housing is arranged for compressing a flange of the one-way expulsion valve against the distal outer periphery of the socket to form a seal therewith.

* * * * *